US006116244A

United States Patent [19]
Hossack et al.

[11] Patent Number: 6,116,244
[45] Date of Patent: Sep. 12, 2000

[54] ULTRASONIC SYSTEM AND METHOD FOR THREE-DIMENSIONAL IMAGING WITH OPACITY CONTROL

[75] Inventors: John A. Hossack, Palo Alto; Ismayil M. Guracar, Redwood City; Joan C. Main, Mt. View, all of Calif.

[73] Assignee: Acuson Corporation, Mountain View, Calif.

[21] Appl. No.: 09/089,468

[22] Filed: Jun. 2, 1998

[51] Int. Cl.$^7$ .................................................... A61B 8/00
[52] U.S. Cl. ............................................ 128/916; 600/441
[58] Field of Search ..................................... 600/437–447, 600/449, 440, 441; 128/916; 382/264; 364/413.13, 413.25; 73/625, 626

[56] References Cited

U.S. PATENT DOCUMENTS

| | | |
|---|---|---|
| 3,617,994 | 11/1971 | Glenn, Jr. et al. . |
| 3,771,116 | 11/1973 | Farrah . |
| 4,100,916 | 7/1978 | King . |
| 4,290,310 | 9/1981 | Anderson . |
| 4,322,974 | 4/1982 | Abele et al. . |
| 4,445,379 | 5/1984 | Yamaguchi et al. . |
| 4,475,397 | 10/1984 | Riley et al. . |
| 4,534,221 | 8/1985 | Fife et al. . |
| 4,662,222 | 5/1987 | Johnson . |
| 4,694,699 | 9/1987 | Cheeke . |
| 4,783,839 | 11/1988 | Bamber . |
| 4,803,994 | 2/1989 | Burke . |
| 4,849,692 | 7/1989 | Blood . |
| 4,872,346 | 10/1989 | Kelly-Fry et al. . |
| 4,913,157 | 4/1990 | Pratt, Jr. et al. . |
| 4,932,415 | 6/1990 | Angelsen et al. . |
| 4,945,305 | 7/1990 | Blood . |
| 5,111,823 | 5/1992 | Cohen . |
| 5,127,409 | 7/1992 | Daigle . |
| 5,159,931 | 11/1992 | Pini . |
| 5,165,413 | 11/1992 | Maslak et al. . |

(List continued on next page.)

FOREIGN PATENT DOCUMENTS

| | | |
|---|---|---|
| 0770352A1 | 5/1997 | European Pat. Off. . |
| 0797106A2 | 9/1997 | European Pat. Off. . |

OTHER PUBLICATIONS

Foley, et al. (1996) "Viewing in 3D", *Computer Graphics Principles and Practice*, pp. 229–283.

Lorenson, et al. (Jul. 1987) "Marching Cubes: A High Resolution 3D Surface Construction Algorithm " *Computer Graphics* vol. 21, No. 4, pp. 163–169.

McCann, et al. (Sep. 1988) "Multidimensional Ultrasonic Imaging for Cardiology" *Proceedings of the IEEE*, vol. 76, No. 9, pp. 1063–1072.

Melton, et al. (1992) "Real–Time Automatic Boundary Detection in Echocardiography" 1992 *Ultrasonics Symposium*, pp. 1113–1117.

(List continued on next page.)

*Primary Examiner*—Marvin M. Lateef
*Assistant Examiner*—Ali M. Imam
*Attorney, Agent, or Firm*—Craig A. Summerfield, Esq.; Brinks Hofer Gilson & Lione

[57] ABSTRACT

A method and system for generating three-dimensional representations using opacity modulation are provided. The opacity level associated with each datum in a 3D volume data set is controlled as a function of at least one Doppler parameter, such as variance. Areas of high variance are assigned a higher level of opacity than areas of low variance. For a Doppler velocity image, velocities associated with high variance are displayed more opaquely than velocities associated with low variance, thereby emphasizing the more opaque regions. The more transparent velocities (i.e., those associated with low variance) still contribute to the image and are displayed. Other Doppler parameters may be used for the image, such as energy, tissue motion or variance. Furthermore, other Doppler parameters may be used to control the opacity, such as velocity, energy or tissue motion.

17 Claims, 3 Drawing Sheets

U.S. PATENT DOCUMENTS

| | | |
|---|---|---|
| 5,187,687 | 2/1993 | Burckhardt et al. . |
| 5,259,384 | 11/1993 | Kaufman et al. . |
| 5,305,756 | 4/1994 | Entrekin et al. . |
| 5,329,496 | 7/1994 | Smith . |
| 5,329,929 | 7/1994 | Sato et al. . |
| 5,353,220 | 10/1994 | Ito et al. . |
| 5,353,354 | 10/1994 | Keller et al. . |
| 5,357,964 | 10/1994 | Spivey et al. . |
| 5,379,642 | 1/1995 | Reckwerdt et al. . |
| 5,379,770 | 1/1995 | Van Veen . |
| 5,396,890 | 3/1995 | Weng . |
| 5,438,998 | 8/1995 | Hanafy . |
| 5,454,371 | 10/1995 | Fenster et al. . |
| 5,474,073 | 12/1995 | Schwartz et al. . |
| 5,479,926 | 1/1996 | Ustuner et al. . |
| 5,485,842 | 1/1996 | Quistgaard . |
| 5,490,512 | 2/1996 | Kwon et al. . |
| 5,503,153 | 4/1996 | Liu et al. . |
| 5,526,816 | 6/1996 | Arditi . |
| 5,546,807 | 8/1996 | Oxaal et al. . |
| 5,562,095 | 10/1996 | Downey et al. . |
| 5,562,096 | 10/1996 | Hossack et al. . |
| 5,566,674 | 10/1996 | Weng . |
| 5,575,286 | 11/1996 | Weng et al. . |
| 5,575,290 | 11/1996 | Teo et al. . |
| 5,582,173 | 12/1996 | Li . |
| 5,600,675 | 2/1997 | Engeler . |
| 5,615,679 | 4/1997 | Ri et al. . |
| 5,623,928 | 4/1997 | Wright et al. . |
| 5,653,235 | 8/1997 | Teo . |
| 5,655,535 | 8/1997 | Friemel et al. . |
| 5,662,116 | 9/1997 | Kondo et al. . |
| 5,667,373 | 9/1997 | Wright et al. . |
| 5,669,385 | 9/1997 | Pesque et al. . |
| 5,671,746 | 9/1997 | Dreschel et al. . |
| 5,678,544 | 10/1997 | DeLonzor et al. . |
| 5,713,356 | 2/1998 | Kruger . |
| 5,720,291 | 2/1998 | Schwartz . |
| 5,740,128 | 4/1998 | Hossack et al. . |
| 5,793,701 | 8/1998 | Wright et al. . |
| 5,860,924 | 1/1999 | Quistgaard .............................. 600/441 |
| 5,961,460 | 10/1999 | Guracar et al. .......................... 600/440 |

OTHER PUBLICATIONS

Sapoznikov, et al. (1987) "Left Ventricular Shape, Wall Thickness and Function Based On Three–Dimensional Reconstruction Echocardiography" *Computers in Cardiology*, IEEE Computer Society Press, Cat. CH2476–0, pp. 495–498.

Tamura, et al. (1985) "Three–Dimensional Reconstruction of Echocardiograms Based on Orthogonal Sections" *Pattern Recognition*, vol. 18, No. 2, pp. 115–124.

Abbott, John G. and F.L. Thurstone (1978) "Multi–Scan Processing in a Phased Array Imaging System" *Ultrasonics Symposium Proceedings*, pp. 220–224.

Abbott, John G. and F.L. Thurstone (1979) "Acoustic Speckle: Theory and Experimental Analysis" *Ultrasonic Imaging*, vol. 1, pp. 303–324.

Amir, Israel et al. (Jul. 1986) "Analysis and Comparison of Some Frequency Compounding Algorithms for the Reduction of Ultrasonic Clutter" *IEEE Transactions on Ultrasonics, Ferroelectrics, and Frequency Control*, vol. UFFC–33, No. 4, pp. 402–411.

Carson, P.L. et al. (1992) "Enhanced Color Flow Imaging of Breast Cancer Vasculature: Continuous Wave Doppler and Three–Dimensional Display" *J. Ultrasound Med.*, vol. 11, pp. 377–385.

Carson, Paul L. et al. (1997) "The 3D and 2D Color Flow Display of Breast Masses" *Ultrasound in Med. & Biol.*, vol. 23, No. 6, pp. 837–849.

Elbaum, et al. (Jun. 1972) "A Wavelength Diversity Technique for Reduction of Speckle Size" *Optics Communications*, vol. 5, No. 3, pp. 171–174.

Elbaum, Marek and Paul Diament (Sep. 1976) "SNR in photocounting images of rough objects in partially coherent light" *Applied Optics*, vol. 15, No. 9, pp. 2268–2275.

Entrekin, Robert and H.E. Melton, Jr. (Sep. 1979) "Real Time Speckle Reduction in B–Mode Images" *Ultrasonics Symposium Proceedings*, pp. 169–174.

Foley, et al. (1996) "Algorithms for Visible–line Determining", *Computer Graphics Principles and Practice*, pp. 665–672.

Giesey, Jeffrey J. (Mar. 1992) "Speckle Reduction in Pulse–Echo Ultrasonic Imaging Using a Two–Dimensional Receiving Array" *IEEE Transactions on Ultrasonics, Ferroelectrics, and Frequency Control*, vol. 39, No. 2, pp. 167–173.

King, Gordon S. (Apr. 1979) "Acoustic Imaging for Nondestructive Evaluation" *Proceedings of the IEEE*, vol. 67, No. 4, pp. 510–525.

Li, Pai–Chi and M. O'Donnell (1994) "Elevational Spatial Compounding" *Ultrasonic Imaging*, vol. 16, pp. 176–189.

Magnin, Paul A. et al. (1982) "Frequency Compounding for Speckle Contrast Reduction in Phased Array Images" *Ultrasonic Imaging*, vol. 4, pp. 267–281.

Nanda, Navin C. et al., editors (1997) "Imaging Instrumentation for Constrast" *Advances in Echo Imaging Contrast Enhancement*, $2^{nd}$ed., pp. 147–150.

Parker, Dennis L. and Pryor, T. Allan (1982) "Analysis of B–Scan Speckle Reduction by Resolution Limited Filtering" *Ultrasonic Imaging*, vol. 4, pp. 108–125 .

Schroeder, Will, et al., editors (1998) "Transparency and Alpha Values" *The Visualization Toolkit*, $2^{nd}$ed. pp. 212–214.

Trahey, Gregg et al. (May 1986) "Speckle Pattern Correlation with Lateral Aperture Translation: Experimental Results and Implications for Spatial Compounding" *IEEE Transactions on Ultrasonics, Ferroelectrics, and Frequency Control*, vol. UFFC–33, No. 3, pp. 257–264.

Wagner, Robert F. (Jan. 1988) "Fundamental Correlation Lengths of Coherent Speckle in Medical Ultrasonic Images" *IEEE Transactions on Ultrasonics, Ferroelectrics, and Frequency Control*, vol. 35, No. 1, pp. 34–44.

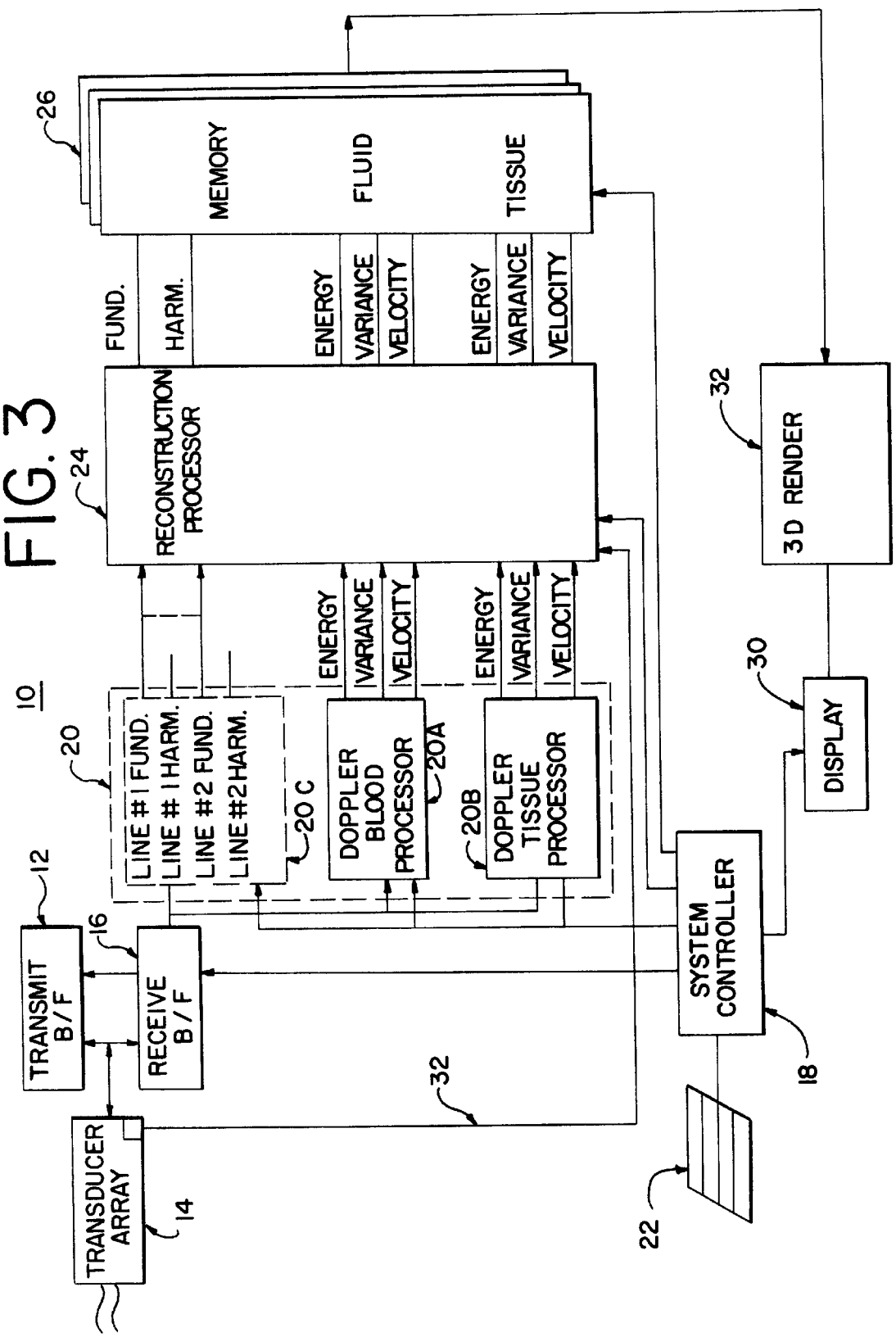

ULTRASONIC SYSTEM AND METHOD FOR THREE-DIMENSIONAL IMAGING WITH OPACITY CONTROL

BACKGROUND

This invention relates to an ultrasound system and method for three-dimensional imaging. In particular, a method and system for controlling opacity for three-dimensional images is provided.

Ultrasound data for various modes of operation are typically used to generate one or more images. Conventional modes of operation include B-mode, color Doppler, Doppler Tissue Motion (see U.S. Pat. No. Re. 35,720) and others.

For three-dimensional imaging, scan converted data used to generate a two-dimensional image may be output to a separate processor or computer. The computer arranges a plurality of sets of data representing two dimensions into a data set representing three-dimensions. Alternatively, a two-dimensional array is used to directly acquire a 3D data set. The data is coded as color or RGB values. A three-dimensional representation is then rendered.

In order to represent the three-dimensional (3D) data set, a two dimensional (2D) image is rendered. For example, a minimum or maximum projection value is displayed. Data along ray lines normal to a viewing plane are compared. The maximum or minimum value along each ray line is displayed opaquely and the other values are translucent (i.e. not displayed).

As another example, each datum is assigned an opacity level corresponding to B-mode intensity, a fixed value, or as a function of depth. The RGB values of each datum are summed as a function of opacity along viewing lines into the 3D data set. However, the relative opacity of various data does not advantageously emphasize some data and de-emphasize other data.

P. L. Carson et al. disclose a "two-dimensional projection of the 3D data [FIG. 5A] in which the depth cue is obtained by decreasing the gray scale pixel brightness as a function of depth (termed 'opacity') along a line of site [sic]. The color pixels representing flow are made completely opaque to maintain maximum flow information." See *Enhanced Color Flow Imaging of Breast Cancer Vasculature: Continuous Wave Doppler and Three-Dimensional Display*, J. Ultrasound Med. 11:377–385 at 382, 1992. Also regarding FIG. 5A, the hue is set based on the Doppler Frequency shifts. See page 384. Carson et al. make a brief statement at page 381 that brightness, hue, saturation, ray attenuation and opacity, and other characteristics were assigned as a function of gray scale pulse echo amplitude and Doppler color (frequency shift signal). This statement is followed by the example for FIG. 5A discussed above.

SUMMARY

The present invention is defined by the following claims, and nothing in this section should be taken as a limitation on those claims. By way of introduction, the preferred embodiment described below includes a method and system for generating three-dimensional representations. The opacity level associated with each datum is controlled as a function of at least one Doppler parameter, such as variance. Areas of high variance are assigned a higher level of opacity than areas of low variance. For a Doppler velocity image, velocities associated with high variance are displayed more opaquely than velocities associated with low variance, emphasizing the high variance (more opaque) regions. The more transparent velocities (i.e., those associated with low variance) still contribute to the image. Other Doppler parameters may be used for the image, such as energy, tissue motion or variance. Furthermore, other Doppler parameters may be used to control the opacity, such as velocity, energy or tissue motion.

Further aspects and advantages are discussed below in conjunction with the preferred embodiments.

BRIEF DESCRIPTION OF THE DRAWINGS

FIG. 3 is block diagram of one embodiment of an ultrasound system for acquiring data for and rendering a 3D image.

DETAILED DESCRIPTION OF PREFERRED EMBODIMENTS

Figure 1:
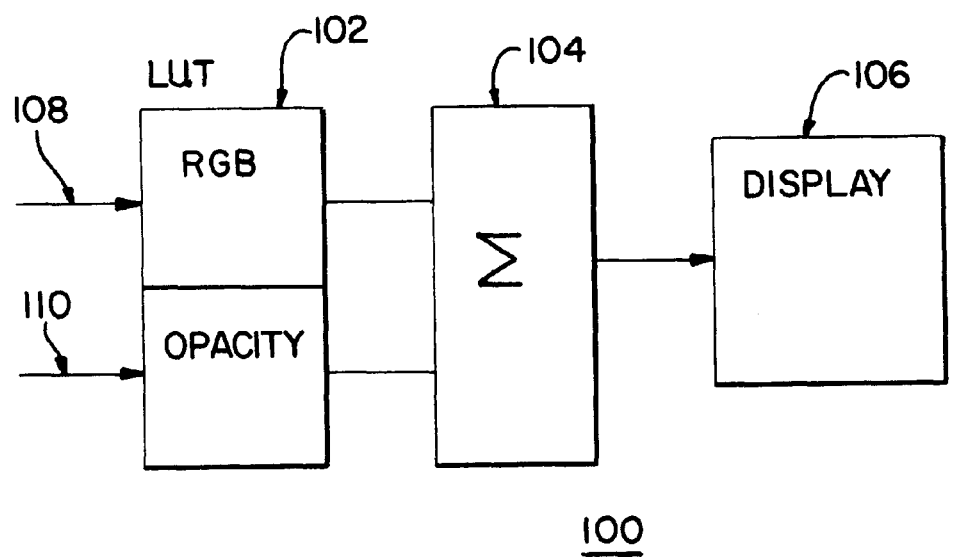
FIG. 1 is a block diagram of one embodiment of an ultrasound system for modulating opacity levels.

The preferred embodiments described below provide versatile opacity control for three-dimensional imaging. Opacity levels associated with data representing a 3D volume are controlled as a function of a Doppler parameter. By controlling the opacity level, some data is rendered more opaque than other data. A display representing the 3D volume emphasizes opaque regions as compared to more transparent regions. Areas of clinical interest, such as a leak in a heart valve or other areas associated with high variance or velocity jets, are emphasized in the display.

The display is associated with one or more of various Doppler modes of processing. Each mode corresponds to a type of Doppler parameter. The modes or parameters include Doppler velocity, energy, variance, tissue motion and combinations thereof. Tissue motion processing includes Doppler velocity, energy or variance parameters filtered or processed to include movement of tissue. Flow processing includes Doppler velocity, energy or variance parameters filtered or processed to include movement of fluids, such as blood. As used herein, Doppler parameter includes any of the tissue motion or flow processing discussed above. Combinations include: (1) one type of parameter displayed as a function of a threshold of another type of parameter, (2) a display associated with a combination of two or more parameters using any of various functions, such as summation or subtraction or modulation functions, and (3) other combinations. Furthermore, one or more of the Doppler parameters may be displayed in combination with B-mode parameters.

Depending on the mode, data associated with one or more Doppler parameters is obtained. The data represents points or regions along one or more scan lines (i.e., lines defined by range gates). For a 2D image, data representing a plurality of scan lines arranged in one of various formats in a plane is obtained. For a 3D image, a set of region data representing a plurality of points, lines or planes in a 3D volume is obtained. For example, multiple sets of 2D data are spatially arranged in parallel or at varying angles within the 3D volume.

Preferably, the data is associated with color values, such as RGB values. Other display color models may be used, such as YUV. The color is selected as a function of the data.

For example, high Doppler energies are displayed as bright red, and low Doppler energies are displayed as light or dull red. As another example, positive Doppler velocities correspond to a range of red colors, and negative Doppler velocities correspond to a range of blue colors. Other color templates may be used, such as yellow, orange, green or other hues and templates which display positive and negative velocities with the same color.

An opacity level is selected for each datum in a set of data representing a set of regions. As used herein, a set of regions includes one or more regions (i.e., spatial locations). As used herein, opacity level includes direct or inverse, linear or nonlinear indications of the relative contribution of data associated with a region to a 2D rendering. Preferably, for each point or region in the 3D volume data set, a color value and corresponding opacity level is assigned. The opacity or α is selected as a value between 0.0 and 1.0.

The opacity level of each datum is selected as a function of one or more Doppler parameters. The same parameter used for the display image or another parameter modulates the opacity level. For example, the opacity level associated with a Doppler velocity image is selected as a function of the Doppler velocity data, Doppler energy data, Doppler variance data, Doppler tissue motion data or combinations thereof. In other examples, other Doppler parameters are used for the display image, such as energy, variance, tissue motion or combinations thereof. Preferably, the opacity is not a fixed value or a function of location (e.g. depth), but may be further modulated by location or another parameter. In one embodiment, opacity is controlled only by one Doppler parameter.

Figure 4:
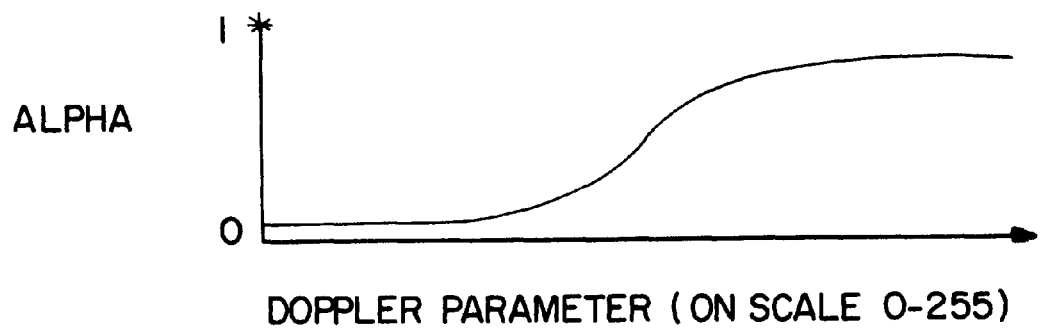
FIG. 4 is a graphic representation of an opacity mapping function.

Any of various functions control the opacity level. For example, a linear function is applied as a mapping function programmed into a look-up table. For an increase in the modulating parameter, the opacity level is linearly increased. Alternatively, a non-linear function is applied. Inverse functions may also be applied, whether linear or non-linear. Inverse mapping may emphasize weak flow in perfused regions, such as emphasizing blood perfusion in the heart muscle and de-emphasizing blood flow in the heart chamber. Other functions may be applied, such as graphically represented in FIG. 4.

Preferably, the opacity level for the display datum associated with each point or region is modulated as a function of data associated with the same point or region. Alternatively, the opacity level is modulated as a function of data associated with a different, larger or smaller region. The opacity level may be selected or controlled at any of various points in the processing path discussed below. For example, the opacity level is controlled before scan conversion into a 2D data set, before conversion into a 3D data set or after conversion into the 3D data set.

Referring to FIG. 1, a schematic diagram of one preferred embodiment of a system for opacity control of 3D images is shown at 100. The system 100 includes a look-up table 102, a summer 104 and a display 106. The look-up table 102 comprises a memory device with a display Doppler parameter input line 108 and an opacity modulation parameter input line 110. In alternative embodiments, the look-up table comprises a processor or filter.

One or more Doppler parameter values for display are input on the input line 108. As discussed above, a color value is assigned as a function of the one or more Doppler parameter values by addressing the look-up table 102. The opacity modulation parameter value is input on the input line 110. Also as discussed above, an opacity level associated with the color value is selected as a function of the parameter. The color value and opacity level for each datum representing the 3D volume is output to the summer 104.

The summer 104 comprises a z-buffer, a memory device, a processor or combinations thereof. The summer 104 converts the 3D data set into a 2D data set representing three-dimensions for display or rendering. Various techniques may be used for rendering, such as volume rendering.

Preferably, color summation is used to render the volume. Based on a range of viewing angles, such as 120 degrees, and the incremental values between each viewing angle, such as 1 degree, multiple two dimensional projections are determined, such as 121. Each projection corresponds to a viewing plane that is perpendicular to a viewing angle. The 3D data samples at each viewing angle are summed along the lines of vision or normal lines "into" the 3D grid or viewing plane to determine a value for each region in the viewing plane.

Color summation is described by W. Schroeder, K. Martin and B. Lorensen in "The Visualization Toolkit," pages 212–214, published by Prentice Hall, 1998. Opacity is represented by α. Therefore, each 3D volume set datum is represented by RGBα.

Figure 2:
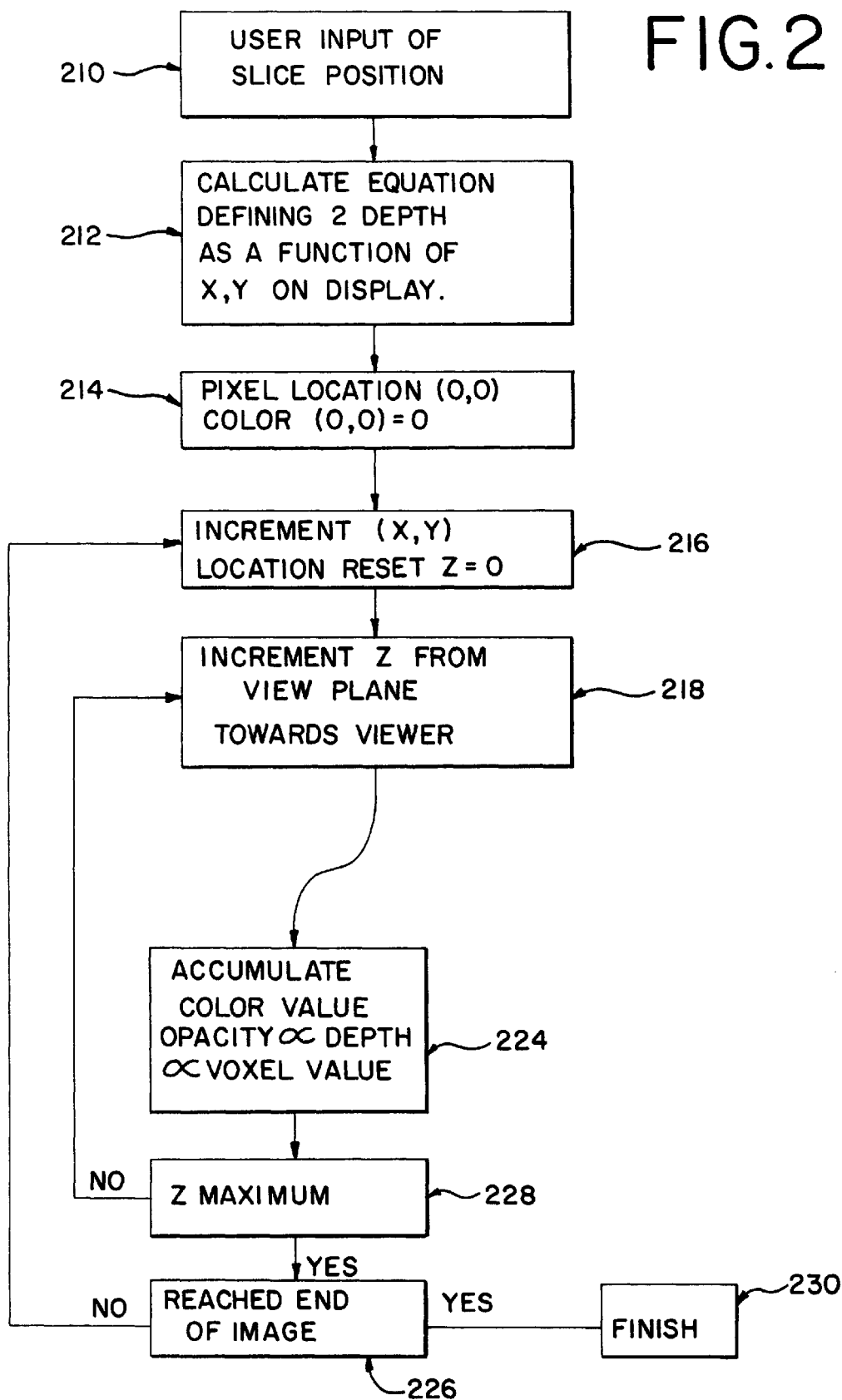
FIG. 2 is a flow chart representing the steps of one embodiment for rendering a 2D data set from a 3D data set with varying opacity levels.

Referring to FIG. 2, one preferred embodiment of a method for color value summation is graphically represented. In step 210, the user inputs a position of the 3D representation (i.e., defines the viewing plane). An equation defining Z-depth as a function of X, Y position on the display is calculated in step 212. In step 214, the color for each 2D display datum or pixel is set to 0.0.

For each X, Y location (pixel), Z is reset to 0 in step 216 (i.e., set farthest from the viewer). Z is incremented from the viewing plane towards the viewer in step 218. The RGBα color information is summed for each increment of Z with the results of the previous summation, $R_T$, $G_T$, $B_T$ and $α_T$ in step 224. The R, G, B and α values are progressively summed in accordance with the following equations:

$$R_{T(N)}=α_N R_N+(1-α_N)R_{T(N-1)} \quad (1)$$

$$G_{T(N)}=α_N G_N+(1-α_N)G_{T(N-1)} \quad (2)$$

$$B_{T(N)}=α_N B_N+(1-α_N)B_{T(N-1)} \quad (3)$$

where T(N) is set to T(N−1) for the next increment of Z.

In step 228, Z is checked to determine whether summation along the viewing line is complete. If Z is not at a maximum value corresponding to a minimum depth from the viewer, Z is incremented in step 218. If Z is at a maximum value, the summation for the viewing line is complete and the process proceeds to step 226. If the values for all the X, Y points or regions of the 2D display data are calculated, the process is finished as designated by step 230. If values for all the X, Y points or regions are not calculated, the process increments to the next X, Y location in step 216.

Referring to FIG. 1, the display value for each X, Y point or region is provided to the display 106. The 2D image representing three-dimensions is displayed to the viewer. Viewer controls may allow for selection of display of various viewing planes.

The volume rendering may include alpha blending, such as depth cueing. For depth cueing, a weighting is applied to each 3D data sample (i.e., each color value and associated opacity or Doppler parameters prior to summation). The weighting values are selected to emphasize near objects. Thus, a sense of front and back regions is created. Alpha blending allows viewing of internal objects relative to surrounding objects. The intensity level associated with each sample may be set as a function of depth, and the opacity may be separately controlled as discussed above (i.e., not weighted as a function of depth).

By modulating the opacity levels associated with the Doppler image parameters, some regions of the 2D display image are emphasized. For example, Doppler variance may indicate turbulent blood flow in the vicinity of a stenosis. By controlling the opacity level associated with Doppler energy, velocity, or variance image data as a function of variance, energy or velocity regions of uniform flow are presented as low opacity (i.e., high translucency) and regions of turbulent flow are presented as high opacity. For a leak in a heart valve encompassed within a large region of moving blood, higher variance exists near the jet (i.e., the leak). The Doppler data relating to the jet is highlighted for easy clinical recognition and quantification and the other Doppler data also contributes to the display. The other Doppler data may provide useful information, such as an aid to orienting insonification for further examination.

Various 3D imaging ultrasound systems may apply opacity control as discussed above. The discussion below describes one alternative ultrasound system with opacity control.

Referring to FIG. 3, a preferred embodiment of an ultrasound system for three-dimensional imaging with opacity control is generally shown at 10. The ultrasound system 10 includes a transmit beamformer 12, a transducer 14, a receive beamformer 16, a system controller 18, a signal processor block 20, and a user interface 22. Remote from the system 10 or included as part of the system 10 are a reconstruction processor 24, a memory 26, and a display 30. A three-dimensional rendering processor 32 may also be included. The ultrasound system 10 is configurable to acquire information corresponding to a plurality of two-dimensional representations or image planes of a subject for three-dimensional reconstruction and imaging. To generate a two-dimensional representation of the subject during an imaging session, the ultrasound system 10 is configured to transmit, receive and process during a plurality of transmit events. Each transmit event corresponds to firing along an ultrasound scan line in the subject.

A. Transmission and Reception

The transmit beamformer 12 is of a construction known in the art, such as a digital or analog based beamformer capable of generating signals at different frequencies. The transmit beamformer 12 generates one or more excitation signals. Each excitation signal has an associated center frequency. Preferably, the center frequency of the excitation signals is within the 1 to 15 MHz range, such as 2 MHz, and is selected to be suitable for the frequency response of the transducer 14. The excitation signals preferably have non-zero bandwidth.

For each or a plurality of transmit events, control signals are provided to the transmit beamformer 12 and the receive beamformer 16 from the system controller 18. The transmit beamformer 12 and transducer 14 are caused to fire one or more acoustic lines for each transmit event. As known in the art, the ultrasonic beams or scan lines are focused in one of various formats, such as linear, steered linear, sector, or Vector®.

For imaging pulsatile targets within the subject (e.g., heart or carotid), gating is preferably used to trigger application of the excitation signals to the transducer 14. In order to further improve three-dimensional imaging, only images corresponding to selected portions of the ECG cycle, the respiratory cycle or both are utilized. Triggering at variable or selectable points in the cycle may also be used.

The transducer 14 is of any construction known in the art, such as the one-dimensional, multiple element (array) Acuson 8L5 transducer or other transducers discussed below. Preferably, the arrays are 1.5 D or plano-concave for obtaining a well-focused elevation beam. Plano-concave transducers are disclosed in U.S. Pat. Nos. 5,678,544 and 5,438,998. Plano-concave transducers may provide improved elevation beam profiles, resulting in reduced artifacts in the 3D image. The transducer 14 converts the excitation signals into ultrasonic energy that is directed along transmit beams into the subject, such as the body of a medical patient. Scattering sites within the subject, such as contrast agents or tissue in the subject, cause echo information to be returned to the transducer 14. The echo may comprise components at fundamental (transmitted) frequencies and possibly components at harmonic frequencies (e.g., twice the fundamental).

Different methods with various transducers may be used for three-dimensional imaging. Three methods for acquiring data for three-dimensional imaging are described below, though other methods may be used. First, a single element transducer (or an axially focused annular array) is mechanically scanned so as to sweep a volume or three-dimensional space. An example of this first method is the method practiced for the Medison-Kretz Combison 530 (Korea). Moving parts for sweeping the volume are enclosed in a fluid filled housing. Thus, the three-dimensional space is swept by mechanically moving the transducer over two-dimensions.

The second method is to use a two-dimensional transducer array to obtain three-dimensional image information directly. A two-dimensional array can be used to scan electronically in any desired orientation to acquire the desired information. Typically, the two-dimensional array is sub-sampled. It is generally impractical to provide a fully sampled 2D array (e.g., 64×64 is 4096 elements). An example of a two-dimensional array is disclosed in U.S. Pat. No. 5,329,496 (Smith). An imaging system for use with the disclosed array is described in U.S. Pat. No. 5,546,807 (Oxaal et al.).

The third method is to collect multiple two-dimensional image data frames associated with relative positional information using a one-dimensional transducer array. The two-dimensional image data frames or image planes are non-coplanar, such as two or more rotationally offset planes or two or more parallel planes offset in elevational position. The positional information provides the relative position among the image data frames so that these frames may be subsequently assembled in a three-dimensional volume to form the desired three-dimensional reconstruction. One dimension is electronically scanned and another dimension is mechanically scanned by rotation, translation, or any combination thereof. For example, the transducer is swept. Sweeping corresponds to rotating the transducer about an axis along the azimuth of the lens surface.

One approach for this third method is to use manual motion detection techniques based on analysis of ultrasonic images. See Tamura et al., "Three-Dimensional Reconstruction of Echocardiograms Based on Orthogonal Sections" (Pattern Recognition, 18, 2, pp. 115–124, 1985).

Another approach is to sense position based on image motion detection, such as disclosed in MULTIPLE ULTRASOUND IMAGE REGISTRATION SYSTEM, METHOD AND TRANSDUCER, U.S. application Ser. No. 08/621,561 (filed Mar. 25, 1996), Ser. No. 08/807,498 (filed Feb. 27, 1997) and Ser. No. 08/916,585 (filed Aug. 22, 1997) to Hossack et al. See also U.S. Pat. No. 5,127,409 to Daigle. The position information is calculated from scan data.

U.S. Pat. No. 5,474,073 to Schwartz describes a qualitative three-dimensional approach using a hand-held transducer array and an assumed scan motion. The transducer is moved manually by free hand motion. The spacing between each two-dimensional image is assumed to be equal.

U.S. Pat. No. 5,353,354 to Keller discloses yet another approach. Accelerometers or magnetic sensors on a transducer measure the position and orientation of the transducer, and, therefore, relative motion between respective image planes. The free hand movement of the transducer is monitored. Suitable magnetic positioning sensors are described in U.S. Pat. Nos. 4,945,305 and 4,849,692 to Blood. Preferably, a pulsed DC type position sensor is used for this type of transducer. Such systems include the mini Bird™ and Flock of Birds™ systems by Ascension Technology Corp. of Burlington, Vt. Alternatively, the 3Space Fastrak from Polhemus (Colchester, Vt.) is used.

Mechanical manipulation guides or fixtures capable of rotation, translation, or a fan-like sweep may also be used to spatially orient each two-dimensional image plane. Such devices are disclosed in U.S. Pat. No. 5,454,371 (Fenster) and U.S. Pat. No. 5,562,095 (Downey et al.).

Another approach is to provide a spaced arrangement of LEDs, such as infra-red LEDs, on the transducer. The LEDs are activated in sequence and monitored with one, or preferably more, cameras. The position and orientation is then inferred from an image of the LEDs generated by the cameras. One such device is manufactured by Image Guided Technologies Inc., Boulder, Colo.

Still another approach is to use a spaced arrangement of microphones. See King U.S. Pat. No. 4,100,916. The position information is determined from the time of flight of acoustic impulses generated by a source on the transducer to the various microphones.

Yet another approach for acquiring multiple two-dimensional frames of data and positional information is to use a motorized array to collect the desired set of image data frames by precisely controlling the movement of the transducer array. One example is the Acuson V5M Transesophageal transducer, a rotating transducer. The rotating transducer produces two-dimensional images at known angles of rotation. A lens design for such a transducer is shown in U.S. Pat. No. 5,562,096 (Hossack, et al.). Another example is a transthoracic transducer, such as disclosed in U.S. Pat. No. 5,159,931 to Pini. See also, Sapoznikov et al., "Left Ventricular Shape, Wall Thickness and Function Based on Three-Dimensional Reconstruction Echocardiography", Computers in Cardiology, IEEE Computer Society Press, Cat CH 2476-0, pp. 495–498, 1987. A related approach is to use a large rotating transducer as described in McCann et al., "Multidimensional Ultrasonic Imaging for Cardiology", Proceedings of IEEE, 76, 9, pp. 1063–1072, September 1988. For example and preferably for use with harmonic imaging, an Acuson 3V2c or 4V2c transducer is placed in a rotatable fixture, such as disclosed in Pini or McCann.

To obtain data for an image, echo signals are received by the transducer 14. This echo information is converted by the transducer 14 into electrical signals that are applied to the receive beamformer 16.

The receive beamformer 16 is of a construction known in the art, such as an analog or digital receive beamformer capable of processing signals associated with different frequencies. The receive beamformer 16 and the transmit beamformer 12 may comprise a single device. The receive beamformer 16 is caused to generate in phase and quadrature (I and Q) information along one or more scan lines. Alternatively, RF signals may be generated. A complete frame of I and Q information corresponding to a two-dimensional representation (a plurality of scan lines) is preferably acquired before I and Q information for the next frame is acquired (the frames are sequentially acquired).

As known in the art, the electrical signals from the transducer 14 are delayed, apodized, and summed with other electrical signals to generate the I and Q information. An ongoing stream of summed signals represents the ultrasound beam or line received from the body, or portions of the lines when multiple transmit focus depths per line are used.

The receive beamformer 16 also performs filtering and passes information associated with a desired frequency band. Two or three-dimensional images are based on receiving signals at various frequencies, such as a fundamental frequency or a harmonic frequency band associated with a fundamental transmit frequency band. Harmonic frequencies are frequencies associated with non-linear propagation or scattering of transmit signals. As used herein, harmonic includes subharmonics as well as second, third, fourth, and other higher harmonics. The harmonic frequency band may overlap the fundamental frequency band.

B. Acoustic Signal Processing

The signal processor 20 comprises one or more processors for generating various Doppler or B-mode parameters representing regions or points. Preferably, the signal processor 20 comprises a Doppler flow processor 20A, a Doppler Tissue processor 20B and a B-mode processor 20C. Each of these processors is preferably a digital signal processor and operates as known in the art to detect information. The Doppler Tissue and flow processors 20B and 20A may comprise one Doppler processor and a wall filter that outputs interleaved types or a selected type of data. The wall filter filters out low frequency (tissue) signals for Doppler flow processing and performs less filtering to include low frequency tissue signals for Doppler Tissue processing.

The signal processor 20 generates one or more types of data. The types may be selected by a user with the user interface 22, such as a keyboard, analog potentiometers or dedicated switches. The user selects the one or more imaging parameters and one or more opacity control parameters. Alternatively, the controller 18 is programmed to select the opacity control parameters in response to other user selections. In response to the selection, the system controller 18 provides control signals to the signal processor 20. Preferably, the various selected types of data represent the same regions of the patient.

The Doppler flow processor 20A estimates Doppler parameters, such as Doppler velocity, variance of velocity and energy from the I and Q signals. The Doppler Tissue processor 20B also estimates Doppler parameters, such as Doppler tissue velocity, tissue variance of velocity and tissue energy from the I and Q signals.

The B-mode processor 20C generates information representing the intensity of the echo signal associated with the I and Q signals.

A scan converter is included in the signal processor 20. For example, scan conversion steps and detection steps as known in the art and described in U.S. application Ser. No. 08/806,922 are performed as one process. Alternatively, the scan conversion and detection steps are performed separately. The scan converter is of a construction known in the art for arranging the output of the signal processor 20 into two-dimensional representations. Preferably, the scan converter outputs formatted video image data frames. Each of the frames of 2D representations corresponds to a respective receive center frequency (such as a second harmonic center frequency) and a respective parameter (such as Doppler velocities).

C. Reconstruction

The scan converted information generated by the signal processor 20 is provided to a reconstruction processor 24. As an alternative to including the scan converter in the signal processor 20, the reconstruction processor 24 includes the scan converter. For example, line data is provided to the reconstruction processor 24 for three-dimensional imaging.

For three-dimensional imaging, the position information and the frames of data are provided to the reconstruction processor 24 via a cable or other data link. Using the frames of data and positional information, the reconstruction processor 24 generates one or more data sets representing three dimensions (3D data sets or reconstructions).

The various 2D data sets are positioned within a 3D volume as a function of the positional information. Once all the frames have been inserted, intermediate points are calculated using three-dimensional linear interpolation techniques relying on a set of closest known data points (e.g. eight closest known data points) or other techniques. Alternatively, spaced line data, such as that associated with an ultrasound scan line, is used to interpolate to the 3D grid.

One or more 3D data sets may be generated for one or more respective Doppler parameter sets. Data for each point of one set may include information from two or more types of data. For example, the data of one set may correspond to first and second Doppler parameters or RGBα data where α is assigned as discussed above. Alternatively, different parameters, whether as RGB or magnitude information, are stored as different 3D data sets.

D. Visualization

For three-dimensional imaging, the 3D data set is rendered into a three-dimensional representation by the 3D render processor 32. The 3D render processor 32 may comprise the same processor as the combination processor 28 and/or the reconstruction processor 24. Alternatively, a separate processor is used for rendering.

If the opacity levels are not assigned by the signal processor 20, the reconstruction processor 24 or another component of the system 10, the 3D render processor 32 controls the opacity level as discussed above.

Various visualization techniques may be used to represent the 3D volume for the 2D display. The 3D data set is rendered into 2D display data values using any of the various techniques described above. The 2D display may correspond to one or more Doppler parameters. At least one of the Doppler parameters opacity level is controlled as a function of another Doppler parameter. Furthermore, the 2D display may include B-mode information associated with a two-dimensional image, a surface rendering or a volume rendering. The 2D display may correspond to the combination of a display representing three dimensions and a display representing two dimensions. For any of the displays discussed above, Doppler parameter modulation of the opacity levels associated with another Doppler parameter emphasizes some regions and de-emphasizes others. The emphasis may aid in clinical evaluation of a patient.

While the invention has been described above by reference to various embodiments, it will be understood that many changes and modifications can be made without departing from the scope of the invention. For example, different combinations, relationships and processors may be used.

It is therefore intended that the foregoing detailed description be understood as an illustration of the presently preferred embodiments of the invention, and not as a definition of the invention. It is only the following claims, including all equivalents, which are intended to define the scope of this invention.

What is claimed is:

1. A method for generating a three-dimensional representation with an ultrasound system, the method comprising the steps of:

(a) controlling an opacity level from one of at least three levels associated with at least a first Doppler parameter at a set of regions representing at least a portion of a three-dimensional volume as a function of a control parameter selected from the group consisting of: a second Doppler parameter, a third Doppler parameter, the first Doppler parameter in combination with at least one of the second and third Doppler parameters, and combinations thereof; and (b) generating the three-dimensional representation as a function of the first Doppler parameter and the opacity levels associated with the set of regions.

2. The method of claim 1 wherein the first Doppler parameter varies as a function of Doppler energy.

3. The method of claim 1 wherein the first Doppler parameter varies as a function of Doppler velocity.

4. The method of claim 1 wherein the first Doppler parameter varies as a function of Doppler variance.

5. The method of claim 1 wherein the control parameter varies as a function of Doppler energy.

6. The method of claim 1 wherein the control parameter varies as a function of Doppler velocity.

7. The method of claim 1 wherein the control parameter varies as a function of Doppler variance.

8. The method of claim 1 wherein the control parameter varies as a function of the first and second Doppler parameters.

9. The method of claim 1 wherein step (a) comprises the step of increasing the opacity level in response to an increase in the control parameter.

10. The method of claim 1 wherein step (a) comprises the step of controlling the opacity level as an inverse function of the control parameter.

11. The method of claim 1 wherein the set comprises a plurality of regions.

12. The method of claim 1 wherein step (b) comprises the step of emphasizing at least a first one of the regions.

13. The method of claim 12 wherein step (b) comprises displaying information adjacent the first region, the information associated with a lower opacity level than the first region.

14. An ultrasound system for generating a three-dimensional representation on a display, the ultrasound system comprising:

a first processor for controlling an opacity level from one of at least three levels associated with at least a first Doppler parameter at a set of regions representing at least a portion of a three-dimensional volume as a function of a control parameter selected from the group consisting of: a second Doppler parameter, a third Doppler parameter, the first Doppler parameter in combination with at least one of the second and third Doppler parameters, and combinations thereof; and a second processor for generating the three-dimensional representation as a function of the opacity levels associated with the set of regions.

15. A method for generating an image data set for a display of a plurality of regions representing a three-dimensional volume with an ultrasound system, the method comprising the steps of:

(a) determining opacity levels from a range of at least three levels as a function of at least a Doppler parameter different than an imaged parameter;

(b) assigning a first opacity level to at least a first of the plurality of regions; and (c) assigning a second opacity level to at least a second of the plurality of regions.

16. The method of claim 15 wherein the Doppler parameter comprises a parameter selected from the group consisting of: a velocity value, an energy value, a variance value, a tissue motion velocity value, a tissue motion variance value, a tissue motion energy value and combinations thereof.

17. The method of claim 15 further comprising:

(d) displaying the first and second regions as Doppler values selected from the group consisting of: flow velocity, flow energy, flow variance, tissue motion velocity, tissue motion variance, tissue motion energy, and combinations thereof.

* * * * *